United States Patent
Miyashita et al.

(10) Patent No.: US 9,748,490 B2
(45) Date of Patent: Aug. 29, 2017

(54) ORGANIC COMPOUND, ORGANIC LIGHT-EMITTING ELEMENT, AND IMAGE DISPLAY UNIT

(71) Applicant: CANON KABUSHIKI KAISHA, Tokyo (JP)

(72) Inventors: Hirokazu Miyashita, Tokyo (JP); Ryuji Ishii, Yokohama (JP); Masanori Muratsubaki, Hachioji (JP); Masumi Itabashi, Kodaira (JP); Jun Kamatani, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 758 days.

(21) Appl. No.: 14/263,206

(22) Filed: Apr. 28, 2014

(65) Prior Publication Data
US 2014/0319494 A1 Oct. 30, 2014

(30) Foreign Application Priority Data

Apr. 30, 2013 (JP) ................................ 2013-096000

(51) Int. Cl.
| | | |
|---|---|---|
| *C07D 209/82* | (2006.01) | |
| *C07D 209/86* | (2006.01) | |
| *C09K 11/06* | (2006.01) | |
| *H01L 51/50* | (2006.01) | |
| *H01L 51/00* | (2006.01) | |
| *H01L 27/32* | (2006.01) | |

(52) U.S. Cl.
CPC ........ *H01L 51/0058* (2013.01); *C07D 209/82* (2013.01); *C07D 209/86* (2013.01); *C09K 11/06* (2013.01); *H01L 27/3244* (2013.01); *H01L 51/0072* (2013.01); *C09K 2211/1007* (2013.01); *C09K 2211/1011* (2013.01); *C09K 2211/1029* (2013.01); *H01L 51/006* (2013.01); *H01L 51/504* (2013.01); *H01L 51/5012* (2013.01); *H01L 51/5056* (2013.01); *H01L 2251/308* (2013.01)

(58) Field of Classification Search
CPC combination set(s) only.
See application file for complete search history.

(56) References Cited

U.S. PATENT DOCUMENTS

| | | | |
|---|---|---|---|
| 2012/0161615 A1 | 6/2012 | Hong | |
| 2012/0286249 A1 | 11/2012 | Lee | |
| 2013/0043460 A1 | 2/2013 | Cheng | |
| 2013/0048975 A1 | 2/2013 | Hong | |
| 2014/0117326 A1* | 5/2014 | Lee | ........................ C09K 11/06 257/40 |
| 2014/0225073 A1* | 8/2014 | Lee | ..................... H01L 51/0061 257/40 |

FOREIGN PATENT DOCUMENTS

| | | |
|---|---|---|
| CN | 101600777 A | 12/2009 |
| CN | 102452974 A | 5/2012 |
| CN | 102558023 A | 7/2012 |
| KR | 2012-0122897 A | 11/2012 |
| WO | 2013/009095 A1 | 1/2013 |

* cited by examiner

*Primary Examiner* — Michael Barker
*Assistant Examiner* — Amanda L Aguirre
(74) *Attorney, Agent, or Firm* — Canon U.S.A. Inc., IP Division

(57) ABSTRACT

An organic compound contains 8H-naphth[2,1-b]carbazole as the basic skeleton thereof. An organic light-emitting element includes an organic compound layer containing the organic compound. A display device and an image display unit each include the organic light-emitting element. The organic light-emitting element is also used in a lighting device and an image forming apparatus.

13 Claims, 2 Drawing Sheets

ORGANIC COMPOUND, ORGANIC LIGHT-EMITTING ELEMENT, AND IMAGE DISPLAY UNIT

BACKGROUND OF THE INVENTION

Field of the Invention

The present invention relates to a novel organic compound, and to an organic light-emitting element and an image display unit using the same.

Description of the Related Art

An organic light-emitting element (referred to as an organic electroluminescent element or organic EL element) includes a pair of electrodes and an organic compound layer disposed between the electrodes. Electrons and holes are injected into the organic compound layer from the electrodes, thereby producing excitons of the organic luminescent compound in the organic compound layer. When the excitons return to the ground state, the organic light-emitting element emits light.

Recently, a considerable number of studies have been carried out on organic light-emitting elements, mainly with one aim of reducing the driving voltage, thickness and weight of light-emitting devices, and providing a device that can emit a variety of emission wavelengths and respond rapidly.

Organic compounds capable of transporting charges are being developed in order to reduce the driving voltage of an organic light-emitting element, and thus to reduce the power consumption.

For example, International Publication WO 2013/009095 discloses the following compound 1-A, and U.S. Patent Laid-Open No. 2013/0043460 discloses the following compound 1-B.

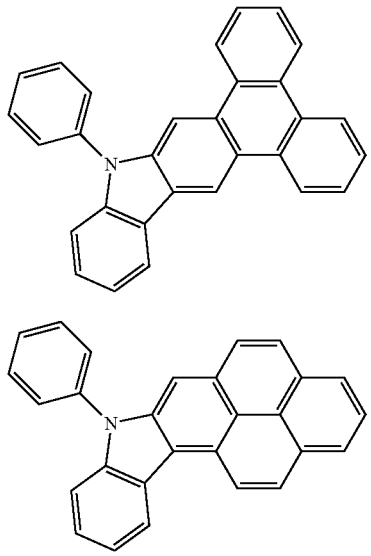

SUMMARY OF THE INVENTION

The present invention provides an organic compound expressed by the following general formula (1):

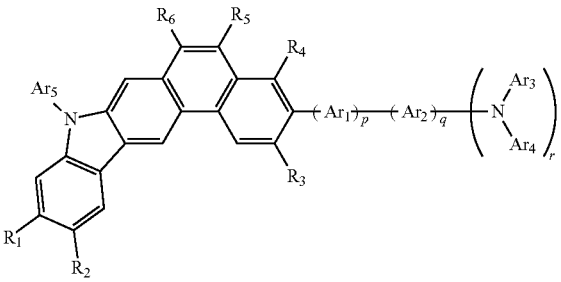

Further features of the present invention will become apparent from the following description of exemplary embodiments with reference to the attached drawing.

DESCRIPTION OF THE EMBODIMENTS

Figure 1:
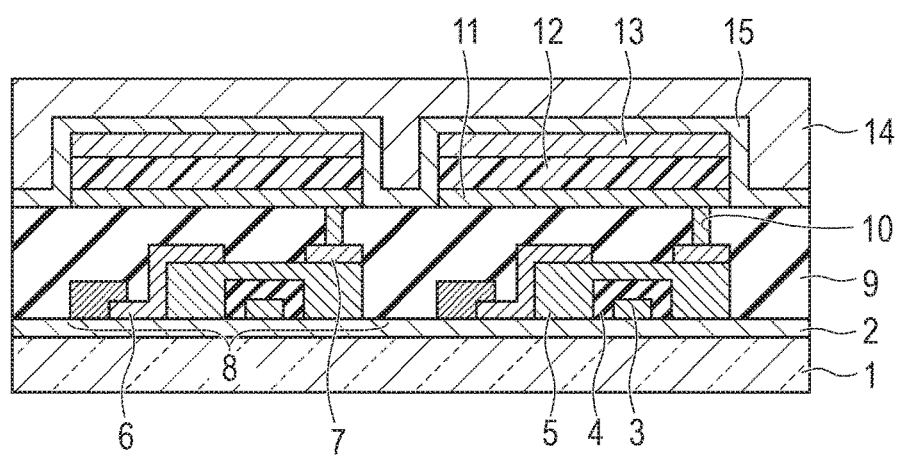
FIG. 1 is a schematic sectional view of a display device including organic light-emitting elements according to an embodiment of the present invention, and transistors each electrically connected to the corresponding organic light-emitting element.

The basic skeletons of the compounds disclosed in International Publication WO 2013/009095 and U.S. Patent Laid-Open No. 2013/0043460 do not exhibit high hole transportability, and have room for improvement.

An organic compound according to an embodiment of the present invention will first be described.

Outline of the Organic Compound

The organic compound of the embodiment of the invention contains 8H-naphth[2,1-b]carbazole as the basic skeleton, as expressed by the following general formula (1):

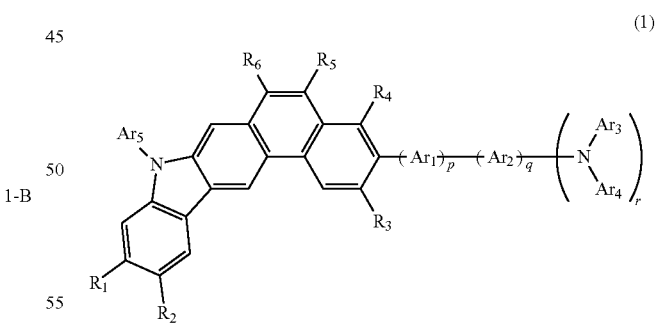

($R_1$ to $R_6$ each represent a chemical species selected from the group consisting of hydrogen, halogens, and cyano, alkyl, and alkoxy groups. $Ar_1$ to $Ar_5$ each represent a group selected from aryl and heterocyclic groups. p, q and r each represent 0 or 1, and all of them are not zero at the same time.)

Exemplary alkyl groups include methyl, ethyl, n-propyl, iso-propyl, n-butyl, iso-butyl, sec-butyl, tert-butyl, n-pentyl, iso-pentyl, tert-pentyl, neopentyl, n-hexyl, and cyclohexyl groups. Methyl and tert-butyl groups may be advantageous.

Exemplary alkoxy groups include methoxy, ethoxy, n-propoxy, iso-propoxy, n-butoxy, iso-butoxy, sec-butoxy, tert-butoxy, n-pentyloxy, and n-hexyloxy. Methoxy and ethoxy groups may be advantageous.

Exemplary aryl groups include phenyl, naphthyl, phenanthryl, anthryl, fluorenyl, acenaphthylenyl, chrysenyl, pyrenyl, triphenylenyl, picenyl, fluoranthenyl, perylenyl, and naphthacenyl groups. Phenyl, naphthyl, phenanthryl, fluorenyl, chrysenyl and triphenylenyl groups may be advantageous.

Exemplary heterocyclic groups include thienyl, pyrrolyl, pyrazinyl, pyridyl, indolyl, quinolyl, isoquinolyl, naphthyridinyl, acridinyl, phenanthrolinyl, carbazolyl, phenazinyl, phenoxazinyl, phenothiazinyl, benzothiophenyl, dibenzothiophenyl, benzofuranyl, dibenzofuranyl, oxazolyl, oxadiazolyl, and naphth[2,1-b]carbazolyl groups. Pyridyl, quinolyl, isoquinolyl, phenanthrolinyl, carbazolyl, dibenzothiophenyl, dibenzofuranyl and naphth[2,1-b]carbazolyl groups are advantageous.

The aryl and heterocyclic groups may have a substituent. Examples of the substituent include halogens, a cyano group, alkyl groups having a carbon number in the range of 1 to 4, and phenyl, naphthyl, phenanthrenyl, fluorenyl, triphenylenyl, chrysenyl, dibenzothienyl, dibenzofuranyl, carbazolyl, and phenanthrolyl groups. It may be advantageous that $Ar_5$ be a phenyl group and that $R_1$ to $R_6$ each represent hydrogen.

It may be advantageous that $Ar_1$ be a phenyl, naphthyl, fluorenyl, phenanthryl, triphenylenyl, pyridyl, phenanthrolinyl, carbazolyl, or naphth[2,1-b]carbazolyl group and that p represent 1.

It may be advantageous that $Ar_2$ be a phenyl, naphthyl, fluorenyl, phenanthryl, triphenylenyl, pyridyl, phenanthrolinyl, carbazolyl, or naphth[2,1-b]carbazolyl group and that q represent 1.

It may be advantageous that $Ar_3$ and $Ar_4$ each be a phenyl, naphthyl, fluorenyl, or phenanthryl group and that r represent 1.

The organic compound expressed by general formula (1) has good linearity and exhibits a high degree of orientation because of the basic skeleton 8H-naphth[2,1-b]carbazole, and accordingly exhibits good charge transportability.

The orientation parameter S of the organic compound satisfies the relationship $-0.50 \leq S < -0.15$. The orientation parameter S mentioned herein is expressed by the following equation:

$$S=(1/2)<3\cos 2\theta-1>=(K_e-K_o)/(K_e+2K_o)$$

In this equation, θ represents the angle between the molecular axis of a thin film (of 10 nm to 100 nm in thickness) of the compound formed on a substrate and the normal of the substrate. $K_o$ and $K_e$ represent the extinction coefficients of the thin film in the directions parallel to and perpendicular to the substrate respectively, measured by variable angle spectroscopic ellipsometry. If all the molecules of the thin film are oriented in the direction parallel to the substrate, the orientation parameter S is −0.50. If the molecules are not oriented and exist at random, S is 0.00. When the orientation parameter S satisfies $-0.50 \leq S < -0.10$, the molecular orbitals of the molecules in the thin film have overlap to a large degree and have good charge transportability.

Variable angle spectroscopic ellipsometry is a method for measuring the extinction coefficient and other optical constants while the incident angle and the wavelength of light are varied. The thin film of the compound may be formed by, for example, vacuum evaporation, spin coating, and a cast method. The orientation of the molecules in the thin film can be evaluated by the known method described in detail in Organic Electronics 10, 127-137 (2009).

Examples of the organic compound are shown below. However, the organic compound is not limited to the compounds below.

A1

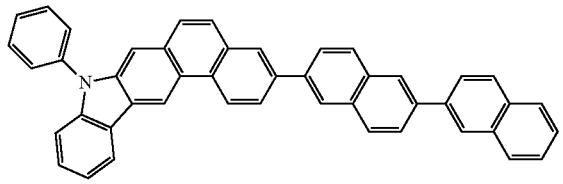

A2

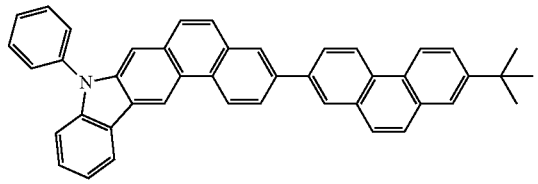

A3

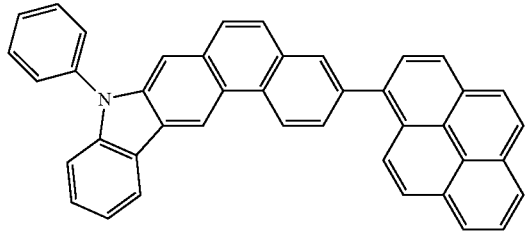

A4

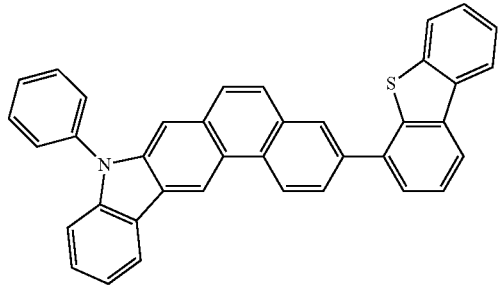

-continued
A5
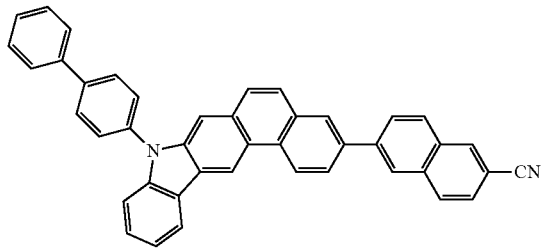
A6
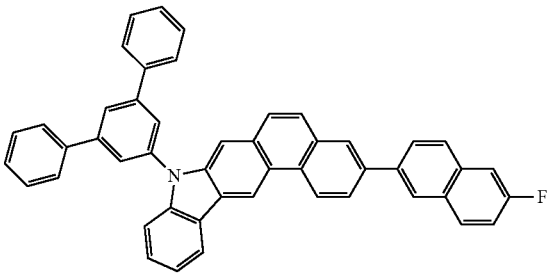
A7
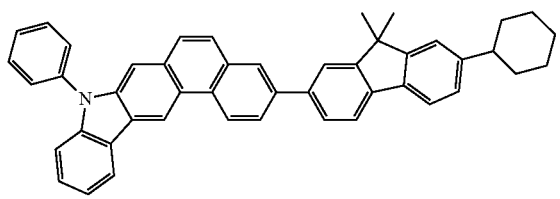
A8
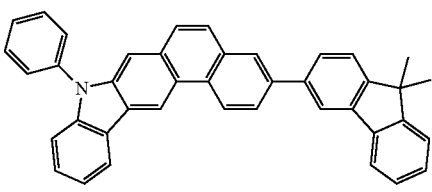
A9
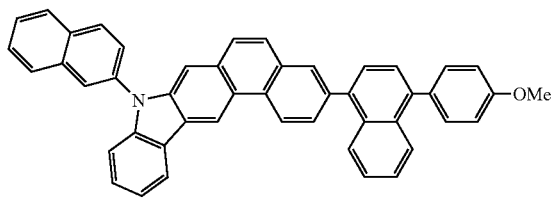
A10
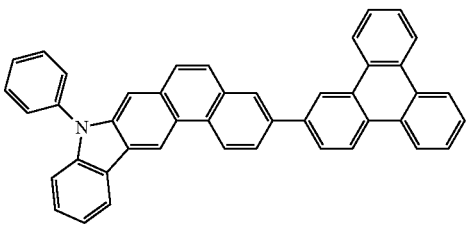
A11
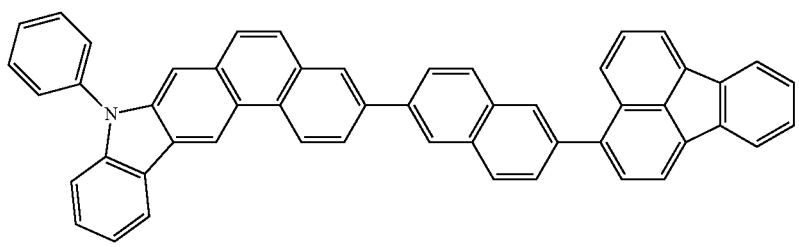
A12
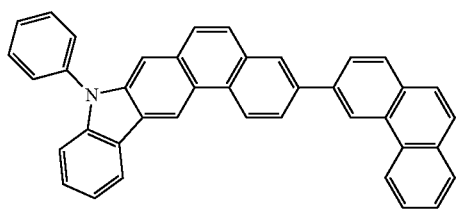
A13
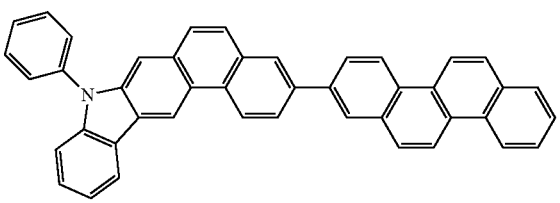
A14
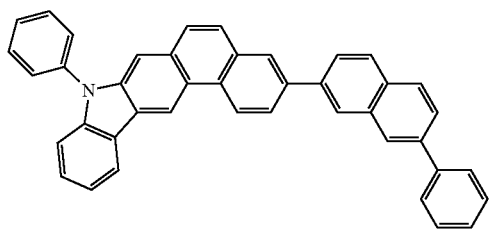
A15
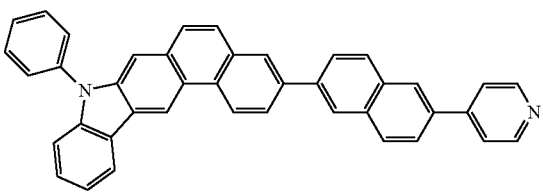

-continued
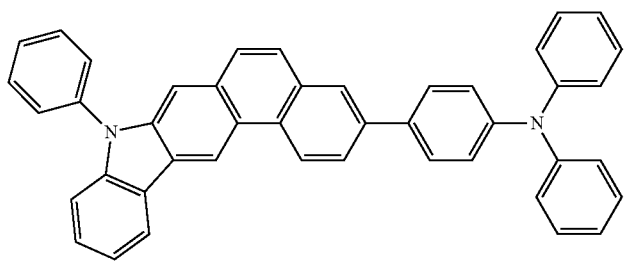
B1
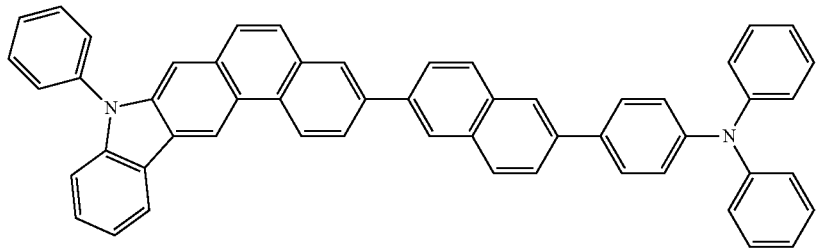
B2
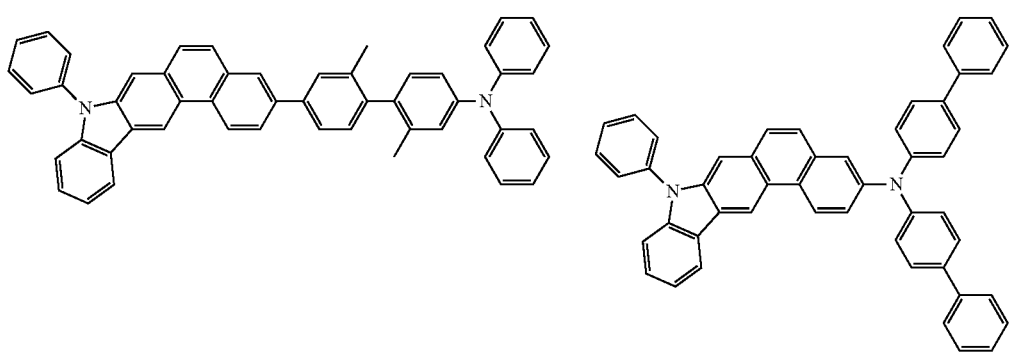
B3    B4
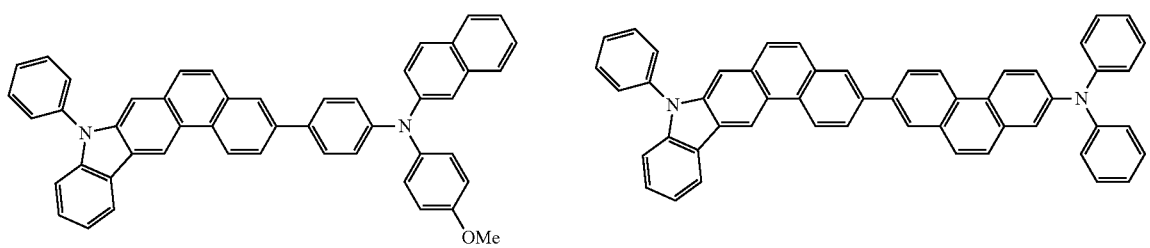
B5    B6
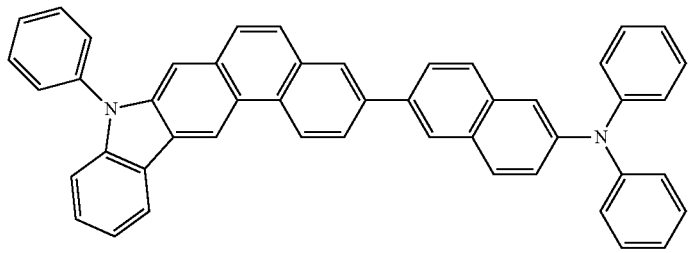
B7

-continued

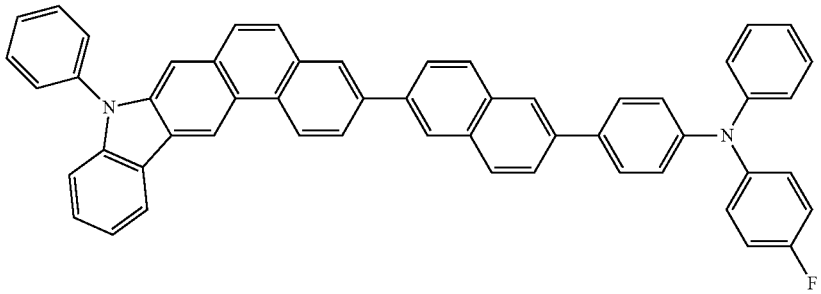
B8

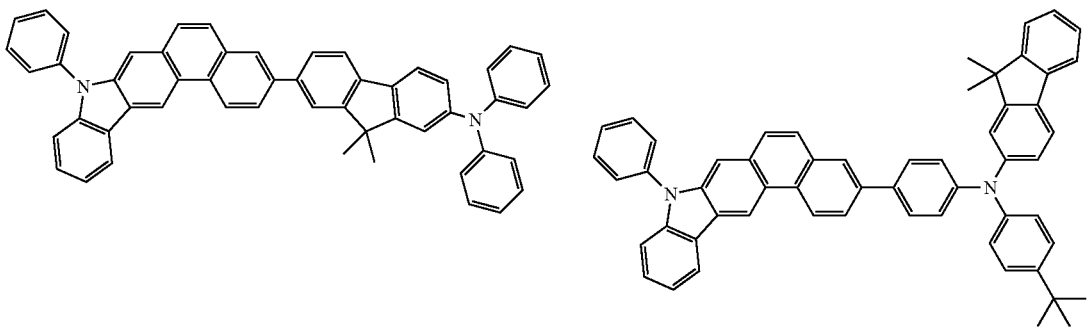
B9  B10

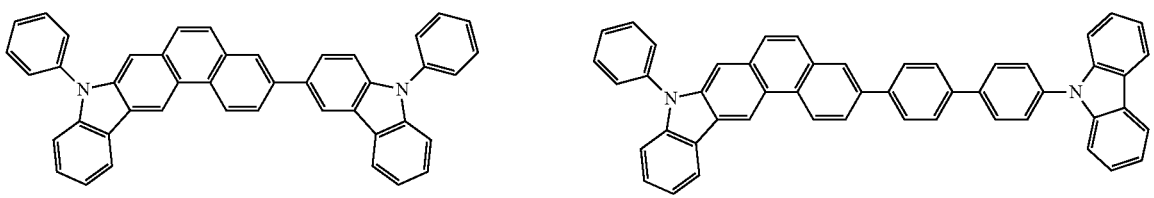
B11  B12

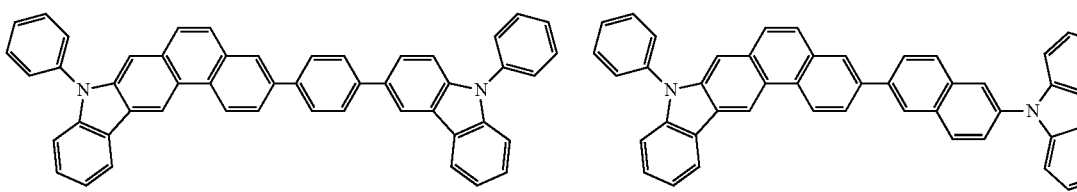
B13  B14

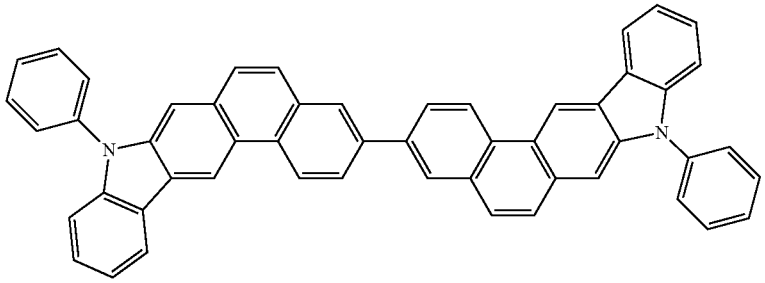
B15

The exemplified compounds of group A, which have a single arylamine site in the molecule, have high oxidation potentials. This implies that the organic compound is stable to oxidation and useful as a hole transport material or a host material.

On the other hand, the exemplified compounds of group B have two arylamine sites in the molecule. These compounds have low oxidation potentials and exhibit high hole mobilities and are accordingly useful as hole injection materials or hole transport materials.

Basic Skeleton

The characteristic features of the basic skeleton of the organic compound of the present embodiment will now be described in comparison with similar compounds. The present inventors think that Compounds 1-A and 1-B cited in the Description of the Related Art are inferior in hole transportability because their molecular orbitals are localized in the basic skeleton, and because the molecules are not easily aligned. On the other hand, the basic skeleton of the organic compound of the present embodiment is 8-phenyl-8H-naphth[2,1-b]carbazole, expressed by the following structural formula (2):

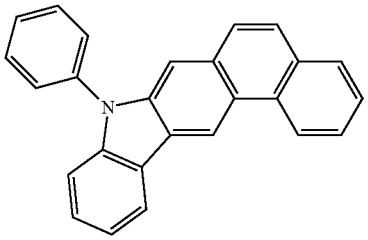

(2)

The basic skeleton of structural formula (2) is compared with the basic skeletons (3) and (4), or compounds 1-A and 1-B.

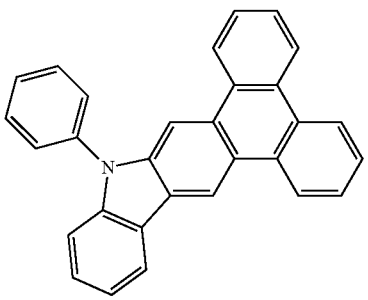

(3)

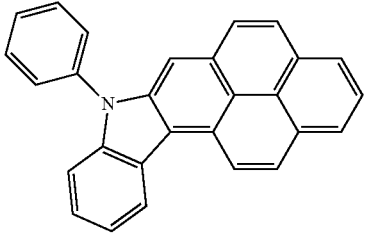

(4)

The relationship between the distribution of molecular orbitals and the charge transportability of a compound will first be described. If the molecular orbitals of an organic compound are localized, a site having a low electron density inhibits hopping conduction among molecules. Therefore, the charge transportability of the film formed of the organic compound is reduced. Hence, it is desirable that molecular orbitals be not localized.

The relationship between the molecular orientation of and the charge transportability of a compound will now be described. When the molecules of a compound are oriented in a certain direction, molecular orbitals overlap to a large degree. This helps hopping conduction occur easily and increases the charge transportability of the compound. Thus, it is advantageous that the compound has a molecular structure allowing the molecules to be oriented in a certain direction. In general, as the linearity of a molecular structure is increased, the degree of molecular orientation increases. This is because the molecules of a compound having a higher linearity tend to interact so as to lie in a position parallel to the substrate and thus become easy to be oriented parallel to the substrate.

Figure 2:
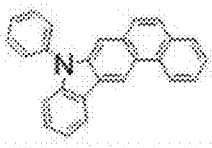
FIG. 2 is a table showing results of calculated molecular orbitals.

The present inventors calculated the molecular orbitals of the above basic skeletons (2) to (4) at the B3LYP/6-31G* level using the density functional theory, and compared the localization of the molecular orbitals and the linearity of the molecular structure among the basic skeletons. The results are shown in Table 1 of FIG. 2.

The calculation for molecular orbitals was performed using Gaussian 03 (Gaussian 03, Revision D. 01, M. J. Frisch, G. W. Trucks, H. B. Schlegel, G. E. Scuseria, M. A. Robb, J. R. Cheeseman, J. A. Montgomery, Jr., T. Vreven, K. N. Kudin, J. C. Burant, J. M. Millam, S. S. Iyengar, J. Tomasi, V. Barone, B. Mennucci, M. Cossi, G. Scalmani, N. Rega, G. A. Petersson, H. Nakatsuji, M. Hada, M. Ehara, K. Toyota, R. Fukuda, J. Hasegawa, M. Ishida, T. Nakajima, Y. Honda, O. Kitao, H. Nakai, M. Klene, X. Li, J. E. Knox, H. P. Hratchian, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, P. Y. Ayala, K. Morokuma, G. A. Voth, P. Salvador, J. J. Dannenberg, V. G. Zakrzewski, S. Dapprich, A. D. Daniels, M. C. Strain, O. Farkas, D. K. Malick, A. D. Rabuck, K. Raghavachari, J. B. Foresman, J. V. Ortiz, Q. Cui, A. G. Baboul, S. Clifford, J. Cioslowski, B. B. Stefanov, G. Liu, A. Liashenko, P. Piskorz, I. Komaromi, R. L. Martin, D. J. Fox, T. Keith, M. A. Al-Laham, C. Y. Peng, A. Nanayakkara, M. Challacombe, P. M. W. Gill, B. Johnson, W. Chen, M. W. Wong, C. Gonzalez, and J. A. Pople, Gaussian, Inc., Wallingford Conn., 2004).

Table 1 shows the structural formulas of the basic skeletons, the spatial distributions of their highest occupied molecule orbitals (HOMO), and the linearities of their molecular structures.

In comparison of the HOMOs involved in transportability, while compounds (3) and (4) each have a site having a low electron density surrounded by dotted line, the orbitals of compound (2) are not localized. Accordingly, compound (2) is superior in hole transportability.

In other words, the organic compound expressed by general formula (1), containing compound (2) as the basic skeleton has good hole transportability.

The linearities of the molecular structures of compounds (2) to (4) were compared at sites having different structures surrounded by dotted rectangular lines. The site of compound (2) surrounded by the dotted line is a phenanthrene skeleton, and the ratio (Lx/Ly) of the longer length (Lx) thereof to the shorter length (Ly) thereof was 1.94. The linearity of a molecular structure increases as Lx/Ly increases. Similarly, the site of compound (3) surrounded by the dotted line is a triphenylene skeleton, and the ratio Lx/Ly was 1.15. The site of compound (4) surrounded by the dotted line is a pyrene skeleton, and the ratio Lx/Ly is 1.43. Thus, the molecules of compound (2) have a larger Lx/Ly value and higher linearity than the molecules of compounds (3) and (4). Accordingly, the molecules of compound (2) are easy to orient in the direction parallel to the surface of the substrate, and the compound is superior in charge transportability.

Hence, the molecules of the organic compound expressed by general formula (1), containing compound (2) as the basic skeleton, are easy to orient in a certain direction and the organic compound is superior in charge transportability. The present inventor believes that the reason why the molecules of a compound having this basic skeleton are easy to orient in a certain direction is that the orientation parameter S of the compound satisfies the relationship $-0.50 \leq S < -0.15$.

The organic compound expressed by general formula (1), which contains 8H-naphth[2,1-b]carbazole as the basic skeleton, exhibits high hole mobility, and the use of this organic compound in an organic light-emitting element reduces the driving voltage of the element.

An organic light-emitting element according to an embodiment will now be described. The organic light-emitting element includes a pair of electrodes (anode and cathode) and an organic compound layer between the electrodes. The organic compound layer may be composed of a single layer or have a multilayer structure including a plurality of layers, as long as it includes a luminescent layer.

If the organic compound layer has a multilayer structure, the multilayer structure may include, for example, a hole injection layer, a hole transport layer, an electron blocking layer, a hole/exciton blocking layer, an electron transport layer and an electron injection layer, in addition to the luminescent layer. Also, the luminescent layer may be composed of a single layer or include a plurality of layers.

In the organic light-emitting element of the present embodiment, at least one layer of the organic compound layer contains the organic compound of general formula (1). More specifically, any of the hole injection layer, the hole transport layer, the electron blocking layer, the luminescent layer, the hole/exciton blocking layer, the electron transport layer, and the electron injection layer contains the organic compound of general formula (1). In an embodiment, it may be advantageous that the hole transport layer contains this organic compound.

If the organic compound is contained in the luminescent layer, the luminescent layer may be made of only the organic compound, or may be made of the organic compound and any other compound. If the luminescent layer is made of the organic compound and any other compound, the organic compound may be used as the host or the guest of the luminescent layer. Alternatively, the organic compound may be used as an assist material in the luminescent layer.

The host mentioned herein refers to a compound accounting for the highest percentage, on a weight basis, of the constituents of the luminescent layer. The guest mentioned herein refers to a compound accounting for a lower percentage, on a weight basis, than the host and acts as the main constituent of the luminescent layer for emitting light. The assist material mentioned herein refers to a compound accounting for the lowest percentage, on a weight basis, of the constituents of the luminescent layer and acting to help emit light. The assist material may be referred to as a second host.

If the organic light-emitting element is a white light-emitting element that emits mixed color light, the luminescent layer may be defined by a single continuous layer or a plurality of separate pieces. The plurality of pieces of the luminescent layer may be disposed on top of one another between the anode and the cathode, or may be arranged in an in-plane direction parallel to the substrate of the light-emitting element.

The present inventors have found that an organic light-emitting element including a hole transport layer containing the organic compound of general formula (1) efficiently emits bright light and has extremely high durability. The hole transport layer may be composed of a single layer or include a plurality of layers. In this instance, the organic light-emitting element may emit any color light without any particular limitation. For example, the organic light-emitting element may emit white light or intermediate color light. The layers of the organic light-emitting element may be formed by evaporation or coating.

In addition to the organic compound, other low-molecular-weight compounds and polymers may be used as required. Low-molecular-weight compounds and polymers may be used as a hole injecting material, a hole transporting material, a host material, a light-emitting material, an electron injecting material, or an electron transporting material.

Examples of these materials are shown below. Compounds having a high hole mobility are suitable as the hole injecting material or the hole transporting material. Examples of the low-molecular-weight or polymeric hole injecting or transporting materials include, but are not limited to, triarylamine derivatives, phenylenediamine derivatives, stilbene derivatives, phthalocyanine derivatives, porphyrin derivatives, polyvinyl carbazole, polythiophene, and other conductive polymers.

Examples of the host material include, but are not limited to, condensed ring compounds, such as fluorene derivatives, naphthalene derivatives, anthracene derivatives, pyrene derivatives, carbazole derivatives, quinoxaline derivatives, and quinoline derivatives; organic aluminum complexes, such as tris(8-quinolinolate) aluminum; organic zinc complexes; and other polymer derivatives, such as triphenylamine derivatives, poly(fluorene) derivatives, and polyphenylene derivatives.

The electron injecting or transporting material is appropriately selected in view of the balance with the hole mobility and other properties of the hole injecting or transporting material. Examples of the electron injecting or transporting material include, but are not limited to, oxadiazole derivatives, oxazole derivatives, pyrazine derivatives, triazole derivatives, triazine derivatives, quinoline derivatives, quinoxaline derivatives, phenanthroline derivatives, and organic aluminum complexes.

For the anode, a conductive material having as high a work function as possible is suitable as the material of the anode. Such materials include elemental metals such as gold, platinum, silver, copper, nickel, palladium, cobalt, selenium, vanadium, and tungsten, and their alloys; and metal oxides such as tin oxide, zinc oxide, indium oxide, indium tin oxide (ITO), and zinc indium oxide. Conductive polymers may be used, such as polyaniline, polypyrrole, and polythiophene. These anode materials may be used singly or in combination. The anode may be composed of a single layer or have a multilayer structure including a plurality of layers.

For the cathode, a conductive material having a low work function is suitable as the material of the cathode. Examples of the cathode material include alkali metals, such as lithium; alkaline-earth metals, such as calcium; and other elemental metals, such as aluminum, titanium, manganese, silver, lead, and chromium. In addition, alloys of these elemental metals may be used. Such alloys include magnesium-silver, aluminum-lithium, and aluminum-magnesium. A metal oxide, such as indium tin oxide (ITO), may be used. These cathode materials may be used singly or in combination. The cathode may be composed of a single layer or have a multilayer structure including a plurality of layers.

The layers of the organic compound layer of the organic light-emitting element, including the layer containing the organic compound of general formula (1) and the other layers containing other organic compounds are formed in the following process. In general, each layer can be formed by vacuum evaporation, ionized evaporation, sputtering, plasma deposition, or a known solution coating method, such as spin coating, dipping, a cast method, a Langmuir-Blodgett (LB) method, or an ink jet method. Layers formed by vacuum evaporation, solution coating or the like are difficult to crystallize and superior in stability with time. For coating, an appropriate binder resin may be used in combination.

Examples of the binder resin include, but are not limited to, polyvinylcarbazole resin, polycarbonate resin, polyester resin, ABS resin, acrylic resin, polyimide resin, phenol resin, epoxy resin, silicone resin, and urea resin. These binder resins may be used in a single form of a homopolymer or copolymer, or in a form of mixture. Known additives, such as a plasticizer, an antioxidant and an ultraviolet light adsorbent, may be used in addition to the binder resin.

The organic light-emitting element may be used as a component of a display device or a lighting device. In addition, the organic light-emitting element may be used in an exposure light source of an electrophotographic image forming apparatus, a backlight of a liquid crystal display device, a color-filterless white light source, or a light-emitting device including a color filter and a white light source. The electrophotographic image forming apparatus may be a copy machine or a laser beam printer, and include an exposure light source and a photosensitive member. The photosensitive member forms a latent image thereon by being exposed to light according to the on/off state of a plurality of organic light-emitting elements of an exposure light source. The on/off state of the organic light-emitting elements is controlled by the corresponding switching elements. The exposure light source includes a plurality of organic light-emitting elements arranged in a line along the longitudinal direction of the photosensitive member. Since the organic light-emitting elements are disposed in a line close to the photosensitive member, the electrophotographic image forming apparatus can be reduced in size.

Color filters each transmit at least one color of red, green and blue. The light-emitting device may include a filter for controlling the chromaticity of white light and a white light source in combination.

The display device includes a display portion including the organic light-emitting elements of an embodiment of the invention. The display portion includes a plurality of pixels. Each pixel includes the organic light-emitting element of an embodiment, and a transistor as a switching element or an amplifier element that controls the luminance of emitted light. The anode and cathode of the organic light-emitting element are electrically connected to one and the other of the drain and source electrodes of the transistor, respectively. The display device can be used as an image display unit of a PC or the like.

Alternatively, the display device may be used in an image display unit including an input portion to which image information is input from an area CCD, a linear CCD, a memory card or the like, and a display portion to which the input image is output. The display device may be a display portion of an image pickup apparatus or ink jet printer. The display portion has functions both as an image output portion on which an image is displayed according to image information input from the outside, and as an operation panel with which information is input to process the image. Also, the display device may be used as a display portion of a multifunction printer.

The lighting device illuminates, for example, a room. The lighting device may emit white light (including neutral white light), or any other color light of the colors from blue to red. The lighting device may include the organic light-emitting element of an embodiment of the invention and an inverter circuit connected to the organic light-emitting element. White has a color temperature of 4200 K and neutral white has a color temperature of 5000 K. The lighting device may further include a color filter.

The organic compound of general formula (1) can be used in an organic solar cell, an organic TFT, a fluorescent biometric identification material, a film, a filter, and so forth in addition to the use thereof as organic light-emitting element.

A display device including the organic light-emitting element of an embodiment of the invention will now be described with reference to FIG. 1. FIG. 1. is a schematic sectional view of a display device including organic light-emitting elements of an embodiment of the invention and TFT elements, or transistors, electrically connected to the corresponding organic light-emitting elements. FIG. 1. of the display device 20 shows two sets of combinations, each including an organic light-emitting element and a TFT element. This structure will now be described in detail.

The display device 20 shown in FIG. 1 includes a substrate 1 made of glass or the like, and a moisture-proof protective layer 2 over the substrate 1 for protecting the TFT elements 8 or the organic compound layer 12. Reference numeral 3 designates a metal gate electrode 3. Reference numeral 4 designates a gate insulating film 4, and reference numeral 5 designates a semiconductor layer.

Each TFT element 8 includes a semiconductor layer 5, a drain electrode 6, and a source electrode 7. An insulating layer 9 is disposed over the TFT elements 8. Each source electrode 7 is connected to the anode 11 of the corresponding organic light-emitting element through a contact hole 10. The display device is not limited to this structure. Either the anode 11 or the cathode 13 is connected to either the source electrode 7 or the drain electrode 6 of the TFT element 8.

Although the organic compound layer 12 is illustrated as a single layer in FIG. 1, it may include a plurality of layers. Furthermore, a first protective layer 14 and a second protective layer 15 are disposed over the cathode 13 to suppress the degradation of the organic light-emitting element.

In an embodiment, MIM elements may be used as switching elements, instead of the transistors. The transistor may be a thin film transistor including an active layer on the insulating surface of the substrate without being limited to a transistor formed in a monocrystalline silicon wafer. The active layer of the thin film transistor may be made of monocrystalline silicon, amorphous silicon, microcrystalline silicon, or an amorphous oxide semiconductor such as IZO (indium zinc oxide) or IGZO (indium gallium zinc oxide). Thin film transistors are referred to as TFT elements.

EXAMPLES

The present invention will be further described with reference to Examples below. However, the present invention is not limited to the examples disclosed below.

Example 1

Synthesis of Exemplified Compound A1

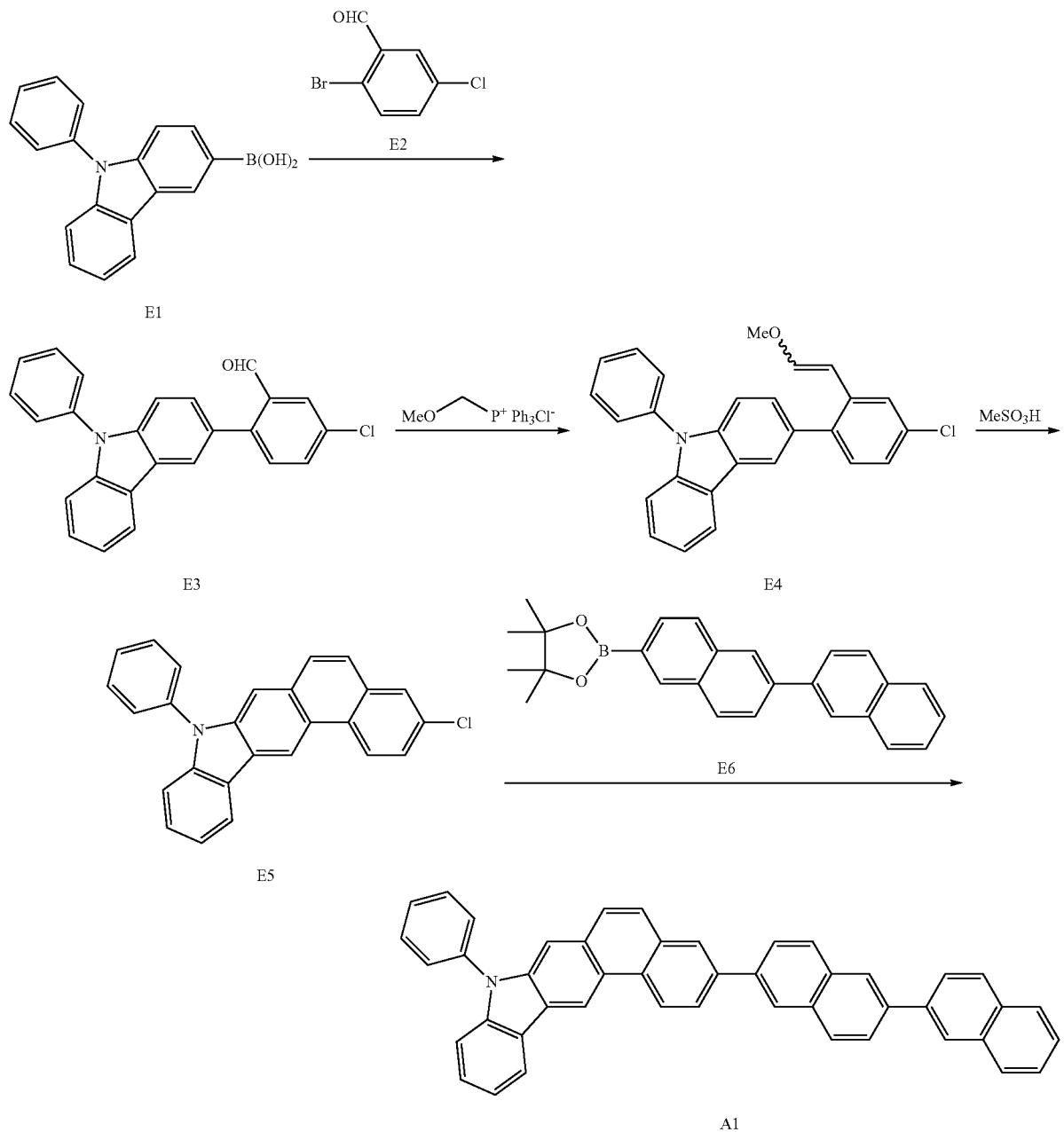

(1) Synthesis of Compound E3

A 300 mL recovery flask was charged with 2.88 g (10 mmol) of compound E1, 2.19 g (10 mmol) of compound E2, 0.1 g of Pd(PPh$_3$)$_4$, 40 mL of toluene, 20 mL of ethanol, and 40 mL of 2 mol/L sodium carbonate aqueous solution. Subsequently, the reaction liquid was heated to 80° C. and stirred for 6 hours in a nitrogen gas flow. After the reaction, toluene was added to the reaction liquid. Subsequently, the organic phase was collected from the reaction liquid by solvent extraction, and then the organic phase was dried using sodium sulfate. Subsequently, the solvent in the organic phase was removed to yield a residue by evaporation under reduced pressure. The residue was purified by dispersion cleaning (solvent: methanol) to yield 3.36 g (yield: 88%) of white solid compound E3.

(2) Synthesis of Compound E4

A 200 mL recovery flask was charged with 7.79 g (22.8 mmol) of (methoxymethyl)triphenylphosphonium chloride and 20 mL of diethyl ether. The reaction liquid was stirred at room temperature for 30 minutes in a nitrogen gas flow. Then, 23 mL of the solution of 12% potassium tert-butoxide in tetrahydrofuran, and 3.00 g (7.85 mmol) of compound E3 were separately added to the reaction liquid in that order, followed by stirring at room temperature for 2 hours in a nitrogen gas flow. After the reaction, water and ethyl acetate were added to the reaction liquid. Subsequently, the organic phase was collected from the reaction liquid by solvent extraction, and then the organic phase was dried using sodium sulfate. Subsequently, the solvent in the organic phase was removed to yield a residue by evaporation under reduced pressure. The residue was purified by silica gel column chromatography (mobile phase:toluene:heptane=1:1) to yield 2.89 g (yield: 90%) of pale yellow oily compound E4.

(3) Synthesis of Compound E5

A 200 mL recovery flask was charged with 1.86 g (4.55 mmol) of compound E4 and 25 mL of dichloromethane. The reaction liquid was stirred at room temperature for 30 minutes in a nitrogen gas flow. To the reaction liquid, 0.44 g (4.55 mmol) of methanesulfonic acid was slowly added, followed by stirring at room temperature for 1 hour in a nitrogen gas flow. After the reaction, methanol was added to the reaction liquid, and a precipitate was collected. The precipitate was purified by dispersion cleaning (solvent: methanol) to yield 1.34 g (yield: 78%) of white solid compound E5.

(4) Synthesis of Exemplified Compound A1

A 100 mL recovery flask was charged with 200 mg (0.53 mmol) of compound E5, 297 mg (0.63 mmol) of compound E6, 87 mg (0.21 mmol) of 2-dicyclohexylphosphino-2',6'-dimethoxybiphenyl, 37 mg (0.06 mmol) of bis(dibenzylideneacetone)palladium (0), 337 mg (1.59 mmol) of tripotassium phosphate, and 10 mL of toluene, and the reaction liquid was stirred at 100° C. for 6 hours in a nitrogen gas flow.

After the reaction, toluene was added to the reaction liquid. Subsequently, the organic phase was collected from the reaction liquid by solvent extraction, and then the organic phase was dried using sodium sulfate.

Subsequently, the solvent in the organic phase was removed to yield a residue by evaporation under reduced pressure. The residue was purified by silica gel column chromatography (mobile phase: chloroform) and further recrystallized (solvent: xylene) to yield 223 mg (yield: 71%) of white solid exemplified compound A1.

Furthermore, 400 mg of the resulting compound A1 was purified to yield 190 mg of highly pure compound A1 by sublimation at a vacuum of $7.0 \times 10^{-1}$ Pa, at a sublimation temperature of 400° C., in an argon gas flow of 10 mL/min in a sublimation purification apparatus manufactured by ULVAC KIKO, Inc.

The resulting compound was identified by matrix-assisted laser desorption/ionization time-of-flight mass spectrometry (MALDI-TOF-MS) using Autoflex LRF manufactured by Bruker.

Measured value: m/z=595.24

Calculated value: $C_{46}H_{29}N$=595.73

Subsequently, compound A1 was deposited onto a silicon substrate subjected to ultrasonic cleaning with pure water, acetone and isopropyl alcohol in a vacuum evaporation apparatus by evaporation at a vacuum of $4 \times 10^{-5}$ Pa and an evaporation rate of 1.0 nm/s, thereby forming a 50 nm thick thin film. The ellipsometry parameters of the resulting thin film were measured at 5° intervals from 45° to 75° at wavelengths in the range of 200 nm to 1000 nm, using a variable angle spectroscopic ellipsometer (manufactured by J. A. Woollam). The measurements were analyzed with a J. A. Woollam software program WVASE 32, and the orientation parameter S was calculated using extinction coefficients $K_e$ and $K_o$. The orientation parameter S of compound A1 was −0.25, suggesting that the molecules of compound A1 were oriented parallel to the substrate.

Example 2

Synthesis of Exemplified Compound B15

Exemplified compound B15 was synthesized in the same manner as in Example 1, except that compound E7 shown below was used instead of compound E6.

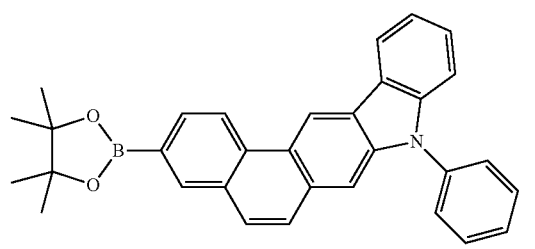

E7

The resulting compound was identified by mass spectrometry.

[MALDI-TOF-MS]

Measured value: m/z=684.44

Calculated value: C52H32N2=684.82

Then, the orientation parameter S of exemplified compound B15 was measured in the same manner as in Example 1, and the result was S=−0.29.

Comparative Example 1

Orientation Parameter Measurement of NPD

The orientation parameter of 4,4'-Bis[N-(1-naphthyl)-N-phenyl]biphenyl (NPD), which is conventionally used as a hole transport material in organic EL elements, was measured in the same manner as in Example 1, and the result was S=−0.02. This suggests that the NPD molecules in the thin film were present at random.

Example 3

In Example 3, an organic light-emitting element was formed which includes an anode, a hole injection layer, a luminescent layer, a hole/exciton blocking layer, an electron transport layer and a cathode, formed on a substrate in that order. The following compounds were used in the present Example.

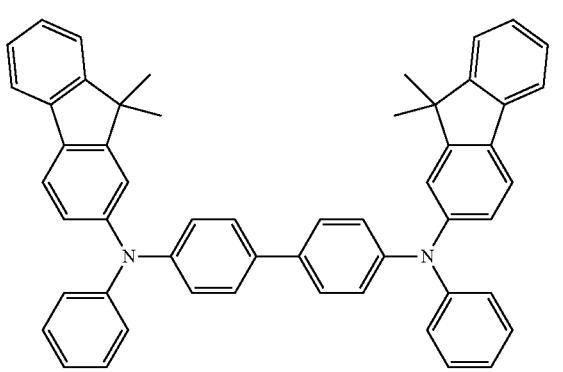

G1

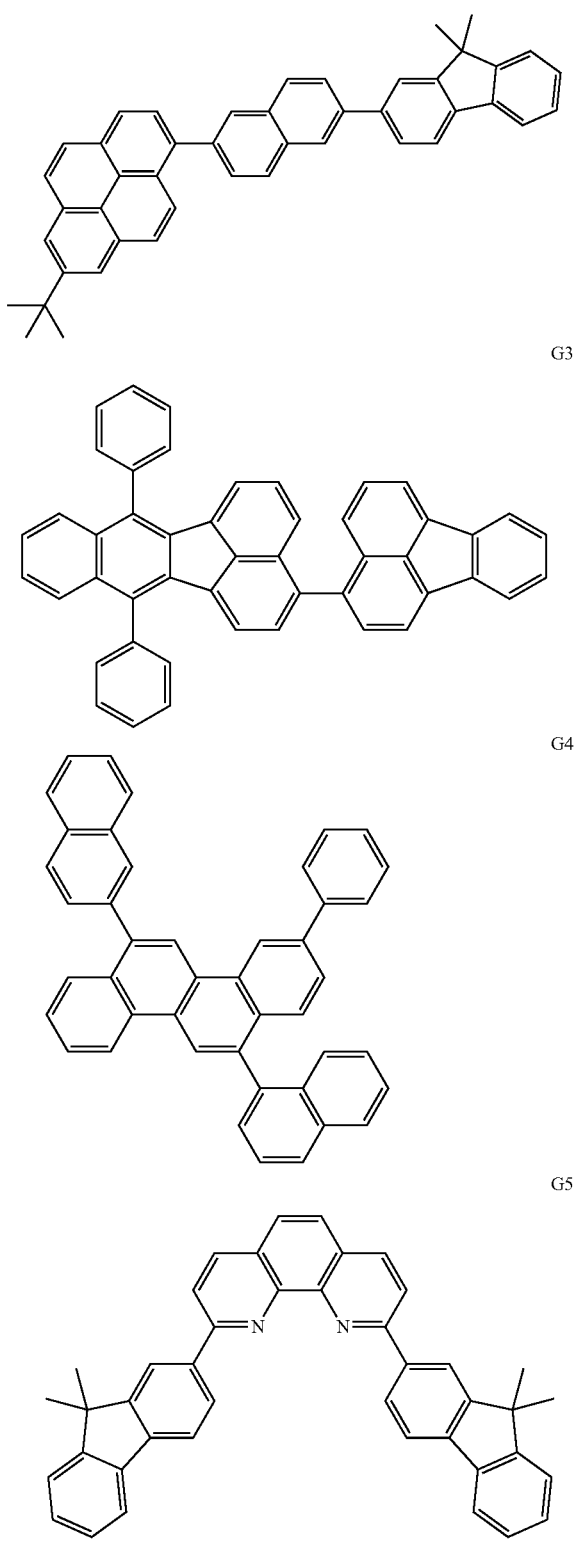

Organic compound layers and electrode layers, shown in Table 2, were continuously formed on the ITO substrate. At this time, the opposing electrode layers (metal electrode layer and cathode) were formed to an area of 3 mm².

TABLE 2

| | Material | Thickness (nm) |
|---|---|---|
| Hole injection layer | G1 | 40 |
| Hole transport layer | Exemplified Compound A1 | 10 |
| Light-emitting layer | G2 (Host) G3 (Guest) G2:G3 = 95:5 (weight ratio) | 30 |
| Hole blocking layer | G4 | 10 |
| Electron transport layer | G5 | 30 |
| First metal electrode layer | LiF | 1 |
| Second metal electrode layer | Al | 100 |

The properties of the resulting element were measured and evaluated. When a voltage of 5.8 V was applied to the ITO electrode (anode) and the Al electrode (cathode), the element emitted blue light having a luminous efficiency of 9.0 cd/A and a luminance of 2000 cd/m². The maximum emission wavelength of the light-emitting element was 460 nm and the chromaticities were (X, Y)=(0.16, 0.24). For the evaluation of stability, the light-emitting element was operated at an initial luminance of 10000 cd/m² and the lifetime until the luminance was 50% reduced was measured. The result exceeded 700 hours. The current-voltage characteristics were measured with a microammeter 4140B manufactured by Hewlett Packard, and the emission luminance was measured with BM7 manufactured by Topcon. The measurement results are shown in Table 3.

Examples 4 to 10

An organic light-emitting element was formed in the same manner as in Example 3 except that compounds of general formula (1) were used as the materials of the hole transport layer or the host. The properties of the resulting element were measured and evaluated in the same manner as in Example 3. The measurement results are shown in Table 3.

TABLE 3

| | Hole transport layer | Host | Luminous efficiency (cd/A) | Voltage (V) | Lifetime until 50% luminous decrease (h) |
|---|---|---|---|---|---|
| Example 3 | A1 | G3 | 9.0 | 5.8 | 700 |
| Example 4 | A4 | G3 | 9.0 | 5.8 | 550 |
| Example 5 | A7 | G3 | 9.1 | 5.8 | 600 |
| Example 6 | B1 | G3 | 9.8 | 5.1 | 500 |
| Example 7 | B2 | G3 | 9.6 | 5.0 | 500 |
| Example 8 | B15 | G3 | 9.5 | 5.1 | 550 |
| Example 9 | B15 | A1 | 9.9 | 4.8 | 450 |
| Example 10 | B1 | A1 | 9.8 | 4.7 | 400 |

Results and Conclusion

By using the novel condensed ring compound of an embodiment of the invention in the hole transport layer or the luminescent layer, as described above, long-life organic light-emitting element that can be operated at a low driving voltage can be provided.

The organic compound of an embodiment of the present invention is superior in charge transportability. By using the organic compound as a material of the organic light-emitting element, the organic light-emitting element can exhibit good emission characteristics.

First, an ITO layer was formed on a glass substrate and then patterned into an ITO electrode (anode). The thickness of the ITO electrode was 100 nm at that time. The resulting substrate having the ITO electrode thereon was used as an ITO substrate in the subsequent step.

Thus, the present invention provides an organic compound that can exhibit good hole transportability. The use of the organic compound leads to an organic light-emitting element that can be operated at a low driving voltage.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-096000, filed Apr. 30, 2013, which is hereby incorporated by reference herein in its entirety.

What is claimed is:

1. An organic compound expressed by the following general formula (1):

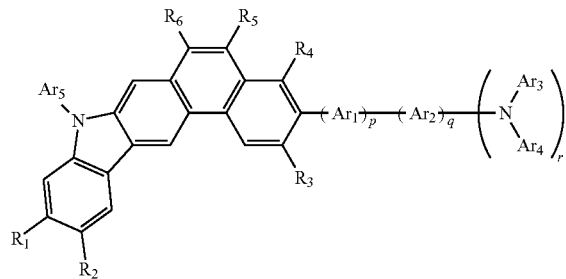

(1)

wherein $R_1$ to $R_6$ each represent a chemical species selected from the group consisting of hydrogen, halogens, and cyano, alkyl, and alkoxy groups; $Ar_1$ to $Ar_5$ each represent a group selected from the group consisting of aryl and heterocycle groups that may each have a substituent selected from the group consisting of halogens, a cyano group, alkyl groups having a carbon number in the range of 1 to 4, phenyl, and naphthyl, phenanthrenyl, fluorenyl, triphenylenyl, chrysenyl, dibenzothienyl, dibenzofuranyl, carbazolyl, and phenanthrolyl groups; and p, q and r each represent 0 or 1, but are not 0 all at the same time.

2. An organic light-emitting element comprising:
an anode;
a cathode; and
an organic compound layer disposed between the anode and the cathode, the organic compound layer containing the organic compound as set forth in claim 1.

3. The organic light-emitting element according to claim 2, wherein the organic compound layer is a luminescent layer.

4. The organic light-emitting device according to claim 2, further comprising a luminescent layer, wherein the organic compound layer is a hole transport layer.

5. The organic light-emitting element according to claim 3, wherein the luminescent layer includes at least two layers that emit different colors.

6. The organic light-emitting element according to claim 5, wherein the organic light-emitting element emits white light.

7. A display device comprising:
a plurality of pixels, each including the organic light-emitting element as set forth in claim 2, and a transistor connected to the organic light-emitting element.

8. A display device comprising:
a plurality of pixels, each including the organic light-emitting element as set forth in claim 5, a transistor connected to the organic light-emitting element, and a color filter.

9. An image display unit comprising:
an input portion to which image information is input; and
a display portion to which an image is output, the display portion including the display device as set forth in claim 7.

10. A lighting device comprising:
the organic light-emitting element as set forth in claim 2; and
an inverter circuit connected to the organic light-emitting element.

11. The lighting device according to claim 10, further comprising a color filter.

12. An image forming apparatus comprising:
a light source including a plurality of the organic light-emitting elements as set forth in claim 2; and
a photosensitive member on which a latent image is formed by exposure using light from the light source.

13. The display device according to claim 7, wherein the transistor contains an oxide semiconductor.

* * * * *